United States Patent
Draber et al.

[11] 3,940,391
[45] Feb. 24, 1976

[54] 3,4-DIHYDRO-1,2,4-TRIAZINE COMPOUNDS

[75] Inventors: Wilfried Draber; Helmut Timmler, both of Wuppertal; Ludwig Eue; Robert R. Schmidt, both of Cologne, all of Germany

[73] Assignee: Bayer Aktiengesellschaft, Leverkusen, Germany

[22] Filed: Aug. 29, 1974

[21] Appl. No.: 502,249

[30] Foreign Application Priority Data
Sept. 18, 1973 Germany............................ 2346936

[52] U.S. Cl.......... 260/248 AS; 71/93; 260/251 QA
[51] Int. Cl.²................................. C07D 253/06
[58] Field of Search................. 260/248 AS

[56] References Cited
UNITED STATES PATENTS
| | | | |
|---|---|---|---|
| 3,544,570 | 12/1970 | Timmler et al. | 260/248 |
| 3,671,523 | 6/1972 | Westphal et al. | 260/248 |
| 3,847,914 | 11/1974 | Dickore et al. | 260/248 |

Primary Examiner—John M. Ford
Attorney, Agent, or Firm—Burgess, Dinklage & Sprung

[57] ABSTRACT

Novel 3,4-dihydro-1,2,4-triazine compounds of the formula

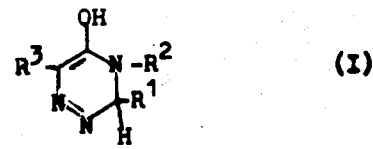

in which
  $R^1$ is alkyl or cycloalkyl;
  $R^2$ is methyl, amino, alkylideneamino, methylamino, β-hydroxyethylamino, 2-furylmethylamino, aralkylamino or substituted aralkylamino; and $R^3$ is alkyl, aryl or substituted aryl;
are prepared by reacting the corresponding 1,2,4-triazin-5-one with sodium borohydride in the presence of a polar solvent at a temperature between −10° and +25°C. The novel compounds are outstandingly effective as herbicides and display particularly selective action.

20 Claims, No Drawings

3,4-DIHYDRO-1,2,4-TRIAZINE COMPOUNDS

The present invention relates to certain novel 3,4-dihydro-1,2,4-triazine compounds and to a process for their preparation. In further aspect, the invention relates to herbicidal compositions containing such compounds and to their use as herbicides.

It is known that 1,6-dihydro-1,2,4-triazines, such as 6-benzyl-3-mercapto-1,6-dihydro-1,2,4-triazin-5-one, can be prepared from compounds such as 6-benzyl-3-mercapto-1,2,4-triazin-5-one by reduction with sodium amalgam (see Bulletin de la Societe chimique de la France 11 (1944), page 273) as in equation (a):

(a)

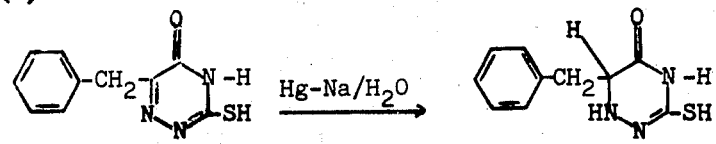

It is also known that 6-membered, N-containing heterocyclic compounds can be reduced with sodium borohydride in aqueous or alcoholic solution, and that thereby at least one of the nitrogencontaining rings is completely hydrogenated but the carbonyl group is not attacked [see U.S. Pat. No. 3,271,396, Helvetica Chimica Acta 50, 1492–1498 (1967) and ibidem 51, 1029–1036 (1968)], as in equations (b) and (c):

(b)

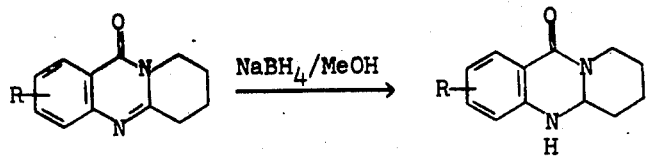

R = N(CH$_3$)$_2$, Cl, C$_2$H$_5$, CH(CH$_3$)$_2$, CF$_3$, OCH$_3$ and the like.

(c)

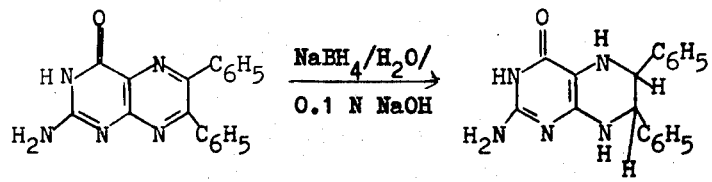

The present invention provides, as new compounds, the 3,4-dihydro-1,2,4-triazines of the general formula

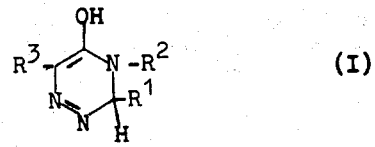  (I)

in which
R$^1$ is alkyl or cycloalkyl;
R$^2$ is methyl, amino, alkylideneamino, methylamino, β-hydroxyethylamino, 2-furylmethylamino, aralkylamino or substituted aralkylamino; and
R$^3$ is alkyl, aryl or substituted aryl.

The new 3,4 dihydro-1,2,4-triazines are distinguished by a good herbicidal activity.

Preferably in formula (I) above, R$^1$ is straight-chain or branched alkyl of from one to six (especially one to four) carbon atoms or cycloalkyl of from three to six (especially three) carbon atoms; R$^2$ is a CH$_3$—, NH$_2$— NHCH$_3$— or NHCH$_2$CH$_2$OH radical, a 2-furylmethylamino radical, an optionally methyl-substituted benzylamino radical, or an alkylideneamino group, the alkylidene moiety of from preferably three to eight (especially three to six) carbon atoms; and R$^3$ is straight-chain or branched alkyl of from one to four carbon atoms or aryl of from six to 10 (especially six) carbon atoms which may carry one or more substituents selected from alkyl of from one to four carbon atoms, halogen (especially chlorine, bromine and fluorine), haloalkyl of from one or two carbon atoms and two to five halogen atoms (especially fluorine), nitro and phenoxy.

The present invention also provides a process for the preparation of a compound of the formula (I) above, in which a 1,2,4-triazin-5-one of the general formula

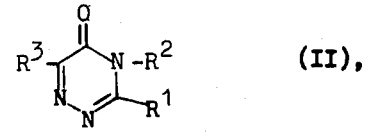  (II), in which

R¹, R² and R³ have the above-mentioned meanings, is reduced with sodium borohydride in the presence of a polar solvent at a temperature between −10° and +25°C, It must be described as distinctly surprising that in the reaction with sodium borohydride, in accordance with the invention, a selective reduction of the carbonyl group in the 1,2,4-triazin-5-one ring takes place, and the second hydrogen atom adds onto the C-3 and not onto the C-5.

The process according to the invention exhibits a number of advantages. Thus, it possesses good reproducibility and gives the compounds of the formula (I) in good purity and high yields. Furthermore, it can easily be carried out industrially since cheap, non-toxic solvents can be used and no great expenditure on apparatus is necessary.

If 3-methyl-4-methylamino-6-phenyl-1,2,4-triazin-5-one is used as the starting compound, the course of the reaction can be represented by the following equation:

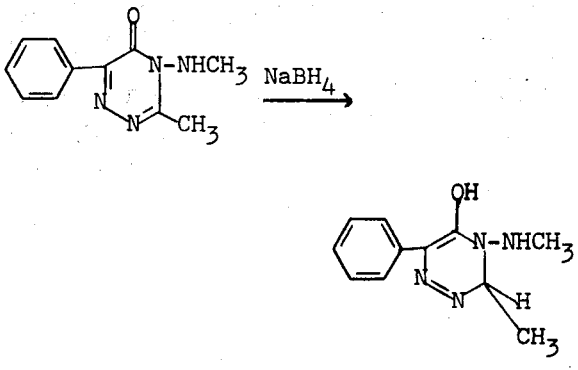

The 1,2,4-triazin-5-ones of the formula (II) in which R² is not alkylideneamino have already been described in the literature [see German Offenlegungsschriften (German Published Specifications) Nos. 2,107,757 and 2,138,031]. The 1,2,4-triazin-5-ones of the formula (II) in which R² is alkylideneamino are the subject of German Published Specification (Offenlegungsschrift) No. 2,238,206 and can be prepared by reacting known 4-amino-5H-1,2,4-triazin-5-ones of the general formula

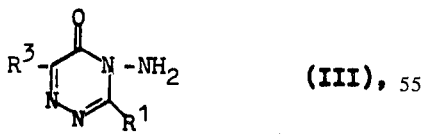

in which

R¹ and R³ have the above-mentioned meanings, with carbonyl compounds of the general formula

in which

R⁴ is hydrogen or alkyl and
R⁵ is alkyl, optionally in the presence of an inert organic solvent, for example a hydrocarbon such as benzene or an ether such as dioxane or tetrahydrofuran, and optionally in the presence of an acid catalyst, for example a Lewis acid such as iron (III) chloride or tin (II) chloride or an organic acid such as p-toluenesulphonic acid, at temperatures between 0° and 120°C (see the preparative Examples hereinafter).

The following may be mentioned as examples of the starting compounds of the formula (II): 3-methyl-4-amino-6-tertiary butyl-1,2,4-triazin-5-one, 3-tertiary butyl-4-amino-6-tertiary butyl-1,2,4-triazin-5-one, 3-isopropyl-4-amino-6-tertiary butyl-1,2,4-triazin-5-one, 3-methyl-4-amino-6-phenyl-1,2,4-triazin-5-one, 3-isopropyl-4-amino-6-phenyl-1,2,4-triazin-5-one,3-methyl-4-amino-6-p-methylphenyl-1,2,4-triazin-5-one,3-methyl-4-amino-6-o-methylphenyl-1,2,4-triazin-5-one, 3-methyl-4-amino-6-m-trifluoromethylphenyl-1,2,4-triazin-5-one, 3-methyl-4-amino-6-o-trifluoromethyl-phenyl-1,2,4-triazin-5-one,3-methyl-4-amino-6-p-trifluoromethylphenyl-1,2,4-triazin-5-one, 3-methyl-4-amino-6-(2′-methyl-4′-chlorophenyl)-1,2,4-triazin-5-one, 3-methyl-4-methylamino-6-phenyl-1,2,4-triazin-5-one,3-methyl-4-benzylamino-6-phenyl-1,2,4-triazin-5-one, 3-methyl-4-isopropylideneamino-6-phenyl-1,2,4-triazin-5-one, 3-methyl-4-isopropylideneamino-6-(2′-methylphenyl)-1,2,4-triazin-5-one,3-methyl-4-methylamino-6-tertiary butyl-1,2,4-triazin-5-one, 3-methyl-4-methyl-6-tertiary butyl-1,2,4-triazin-5-one,3-methyl-4-methyl-6-phenyl-1,2,4-triazin-5-one and 3-isopropyl-4-methyl-6-phenyl-1,2,4-triazin-5-one.

For the preparative process of this invention, the diluent may be any polar organic solvent, especially an ether such as dioxane or tetrahydrofuran, or an alcohol such as methanol and ethanol.

In general, the reaction is carried out at a temperature between −10° and +25°C, preferably between −5° and +10°C.

The reaction can be carried out not only under normal pressure but also under elevated pressure. In general, it is carried out at 1 to 1.5, preferably at 1 to 1.2, atmospheres.

In carrying out the process according to the invention, 1 to 1.2 moles of sodium borohydride are preferably employed per mole of 1,2,4-triazin-5-one of the formula (II). Exceeding the stoichiometric ratio by a greater amount does not produce any significant improvement in yield.

To isolate the active compounds according to the invention, the solvent is distilled off almost to dryness, under reduced pressure, and the residue is taken up in water. The precipitate is filtered off and well washed with warm water. The 3,4-dihydrotriazines according to the invention are as a rule obtained as fine crystalline powders which do not require recrystallization.

The process of this invention and the preparation of the compounds of the invention is illustrated by the following Examples:

EXAMPLE 1

Preparation of 5-hydroxy-3-methyl-4-methyl-amino-6-phenyl-3,4-dihydro-1,2,4-triazine

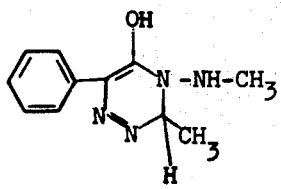 (1)

108 g (0.5 mol) of 3-methyl-4-methylamino-6-phenyl-1,2,4-triazin-5-one were suspended in 1 l of methanol. 19.0 g (0.5 mole) of sodium borohydride were introduced in portions into this suspension at 0° to 10°C, whilst stirring and applying external cooling. After completion of the addition, the mixture was stirred for 4 hours at about 0° to 5°C and then for 8 hours at room temperature. A clear yellow solution was produced, which was freed from the solvent in vacuo. Water was added to the residue and the resulting precipitate was filtered off, thoroughly washed with water and dried. After drying, 90 g (83% of theory) of 5-hydroxy-3-methyl-4-methyl-amino-6-phenyl-3,4-dihydro-1,2,4-triazine of melting point 91°C were obtained.

EXAMPLE 2

Preparation of 3-ethyl-5-hydroxy-4-methyl-6-phenyl-3,4-dihydro-1,2,4-triazine

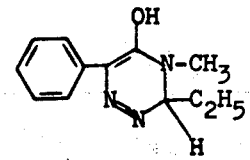 (2)

21.5 g (0.1 mole) of 3-ethyl-4-methyl-6-phenyl-1,2,4-triazin-5-one were suspended in 200 ml of methanol and 4.6 g (0.12 mole) of sodium borohydride were added in portions, whilst cooling with ice. After stirring for several hours whilst cooling with ice, the temperature was allowed to rise to 20°C and the mixture was then stirred for a further 8 hours at room temperature. The resulting solution was partially freed from the solvent under reduced pressure, water was added to the oily residue and the precipitate was filtered off, well washed with water and dried.

18.4 g (85% of theory) of 3-ethyl-5-hydroxy-4-methyl-6-phenyl-3,4-dihydro-1,2,4-triazine of melting point 122°C were obtained.

The compounds listed in Table 1 which follows were prepared by methods analogous to those described in Examples 1 and 2.

Table 1

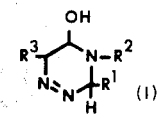 (I)

| Example No. | $R^1$ | $R^2$ | $R^3$ | Melting point (°C) |
|---|---|---|---|---|
| 3 | $CH_3$ | $NH_2$ | phenyl | 135 |
| 4 | $C_2H_5$ | $NH_2$ | phenyl | 101 |
| 5 | $C_2H_5$ | $NH_2$ | phenyl-$CF_3$ | 108 |
| 6 | $C_4H_9$ | $NH_2$ | phenyl | 120 |
| 7 | $C_5H_{11}$ | $NH_2$ | phenyl | 95 |
| 8 | $C_2H_5$ | $NH_2$ | phenyl-Cl | 92 |
| 9 | H | $NH_2$ | $C(CH_3)_3$ | 58–61 |
| 10 | $C_2H_5$ | $NH_2$ | $C(CH_3)_3$ | 114 |
| 11 | $CH(CH_3)_2$ | $NH_2$ | $C(CH_3)_3$ | 183 |
| 12 | $C_2H_5$ | $NH_2$ | phenyl-O-phenyl | 145 |
| 13 | $C_2H_5$ | $NHCH_3$ | $C(CH_3)_2$ | 91 |

Table 1-continued

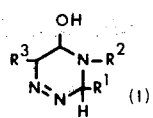

(1)

| Example No. | R¹ | R² | R³ | Melting point (°C) |
|---|---|---|---|---|
| 14 | $C_2H_5$ | $NHCH_3$ | phenyl | 140 |
| 15 | $C_6H_{13}$ | $NHCH_3$ | phenyl | 96 |
| 16 | $CH_3$ | $NHCH_3$ | $(CH_3)_3C$–phenyl– | 134 |
| 17 | $C_2H_5$ | $NHCH_2CH_2OH$ | phenyl | 126 |
| 18 | $CH_3$ | $NHCH_2$–phenyl–$CH_3$ | phenyl | 119 |
| 19 | $CH_3$ | $N=C(CH_3)_2$ | phenyl | 147 |
| 20 | $C_2H_5$ | $N=C(CH_3)_2$ | phenyl | 100 |
| 21 | $C_2H_5$ | $N=C(CH_3)_2$ | phenyl-$CF_3$ | 114 |
| 22 | $C_2H_5$ | $NH_2$ | phenyl-$OCH_3$ | 108 |
| 23 | $CH_3$ | $NHCH_2$–furyl | phenyl | 79 |
| 24 | H (cyclohexyl) | $NH_2$ | phenyl | 175–177 |
| 25 | cyclopropyl | $NHCH_3$ | phenyl | 135 |
| 26 | $C_2H_5$ | $NH_2$ | cyclohexyl (H) | 80 |
| 27 | $C_2H_5$ | $NH_2$ | $CH_3O$–phenyl | 113 |

The preparation of the starting materials (II) is illustrated in the following Example:

(IIa)

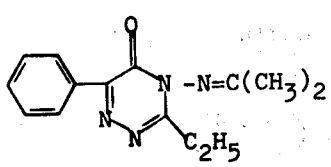

10.8 g (0.05 mole) of 3-ethyl-4-amino-6-phenyl-5H-1,2,4-triazin-5-one (known from DOS (German Published Specification) 2,138,031) were dissolved in 250 ml of acetone and after addition of 0.1 g of p-toluene-sulphonic acid the mixture was heated to the boil under reflux for 1 hour. The reaction solution was filtered hot, the solvent was then partly distilled off and 20 to 50 ml of isopropanol were added to the residue. The crystalline precipitate thereupon obtained was filtered off and washed with ether. 10.9 g (85% of theory) of 3-ethyl-4-propylideneamino-6-phenyl-5-H-1,2,4-triazin-5-one of melting point 146°C were thus obtained.

The following compounds could be prepared analogously:

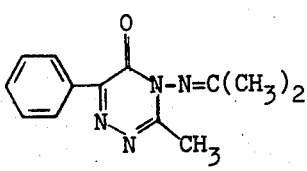

(IIb)   Melting point 99°C

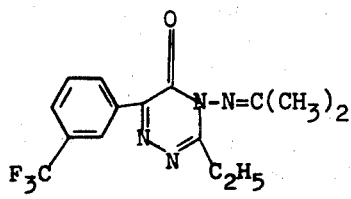

(IIc)   Melting point 136°C

The following may be mentioned as examples of active compounds according to the invention: 3-methyl-4-amino-5-hydroxy-6-phenyl-3,4-dihydro-1,2,4-triazine, 3-methyl-4-methyl-5-hydroxy-6-phenyl-3,4-dihydro-1,2,4-triazine, 3-isopropyl-4-methyl-5-hydroxy-6-phenyl-3,4-dihydro-1,2,4-triazine, 3-methyl-4-amino-5-hydroxy-6-tertiary butyl-3,4-dihydro-1,2,4-triazine, 3-ethyl-4-amino-5-hydroxy-6-phenyl-3,4-dihydro-1,2,4-triazine, 3-isopropyl-4-amino-5-hydroxy-6-phenyl-3,4-dihydro-1,2,4-triazine, 3-methyl-4-methylamino-5-hydroxy-6-phenyl-3,4-dihydro-1,2,4-triazine, 3-methyl-4-amino-5-hydroxy-6-p-methylphenyl-3,4-dihydro-1,2,4-triazine, 3-methyl-4-amino-5-hydroxy-6-(2',4'-dimethoxyphenyl)-3,4-dihydro-1,2,4-triazine and 3-methyl-4-amino-5-hydroxy-6-(4'chlorophenyl)-3,4-dihydro-1,2,4-triazine.

The 3,4-dihydro-1,2,4-triazines according to the invention possess good herbicidal properties and can therefore be used for combating weeds.

Weeds in the broadest sense are to be understood as all plants which grow in locations where they are not desired. Whether the active compounds according to the invention act as total herbicidal agents or as selective herbicidal agents depends on the amount of the active compound used.

The active compounds according to the invention can be used, for example, in the case of the following plants: dicotyledons such as mustard (Sinapis), cress (Lepidium), cleavers (Galium), chickweed (Stellaria), camomile (Matricaria), gallant soldier (Galinsoga), goosefoot (Chenopodium), annual nettle Urtica) and groundsel (Senecio) and Monocotyledons such as timothy (Phleum), bluegrass (Poa), fescue (Festuca), goosegrass (Eleusine), foxtail (Setaria), ryegrass (Lolium), cheat (Bromus), barnyard grass (Echinochloa) and millet (Panicum).

The active compounds according to the invention exert a very strong influence on plant growth, but in different ways, so that they can be used as selective herbicides. They exhibit particular advantages as selective herbicides in crops of cotton, corn and cereals. In higher concentrations, they can also be employed as total herbicides.

The active compounds according to the present invention can be converted into the usual formulations, such as solutions, emulsions, suspensions, powders, pastes and granulates. These may be produced in known manner, for example by mixing the active compounds with extenders, that is, liquid or solid or liquefied gaseous diluents or carriers, optionally with the use of surfaceactive agents, that is, emulsifying agents and/or dispersing agents and/or foam-forming agents. In the case of the use of water as an extender, organic solvents can, for example, also be used as auxiliary solvents.

As liquid diluents or carriers, there are preferably used aromatic hydrocarbons, such as xylenes, toluene, benzene or alkyl naphthalenes, chlorinated aromatic or aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethyl formamide, dimethyl sulphoxide or acetonitrile, as well as water.

By liquefied gaseous diluents or carriers are meant liquids which would be gaseous at normal temperatures and pressures, for example aerosol propellants, such as halogenated hydrocarbons, for example freon.

As solid diluents or carriers, there are preferably used ground natural minerals, such as kaolins, clays, talc, chalk, quartz, attapulgite, montmorillonite or diatomaceous earth, or ground synthetic minerals, such as highly-dispersed silicic acid, alumina or silicates.

Preferred examples of emulsifying and foam-forming agents include non-ionic and anionic emulsifiers, such as polyoxyethylene-fatty acid esters, polyoxyethylene-fatty alcohol ethers, for example alkylarylpolyglycol ethers, alkyl sulphonates, alkyl sulphates and aryl sulphonates as well as albumin hydrolyzation products; and preferred examples of dispersing agents include lignin sulphite waste liquors and methyl cellulose.

The active compounds according to the invention can be present in the formulations as a mixture with other active compounds.

In general, the formulations contain from 0.1 to 95 per cent by weight of active compound, preferably from 0.5 to 90 per cent by weight.

The active compounds can be used as such, in the form of their formulations or as the use forms prepared therefrom, such as ready-to-use solutions, emulsions, suspensions, powders, pastes and granules. They may be used in the customary manner, for example, by watering, spraying, atomizing, scattering and dusting.

They can be used both in accordance with the post-emergence process and in accordance with the pre-emergence process.

The amount of active compound employed can vary within fairly wide ranges: it depends essentially on the nature of the desired effect. In general, the amounts employed are between 0.1 and 20 kg of active compound per ha, preferably between 0.2 and 15 kg/ha.

The present invention also provides a herbicidal composition containing as active ingredient a compound of the present invention in admixture with a solid or liquefied gaseous diluent or carrier or in admixture with a liquid diluent or carrier containing a surface-active agent.

The present invention also provides a method of combating weeds which comprises applying to the weeds or a weed habitat a compound of the present invention alone or in the form of a composition containing as active ingredient a compound of the present invention in admixture with a diluent or carrier.

The present invention further provides means of yielding crops protected from damage by weeds by being grown in areas in which immediately prior to and/or during the time of the growing a compound of the present invention was applied alone or in admixture with a diluent or carrier. It will be seen that the usual methods of providing a harvested crop may be improved by the present invention.

The active compounds according to the invention also exhibit a fungicidal activity, especially against cereal diseases, such as rust.

The good herbicidal activity of the active compounds according to the invention can be seen from the Examples which follow.

EXAMPLE A

Post-emergence test

Solvent: 5 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was then diluted with water to the desired concentration.

Test plants which had a height of 5–15 cm were sprayed with the preparation of the active compound in such a way as to apply the amounts of active compound per unit area which are indicated in the table. Depending on the concentration of the spray liquor, the amount of water used was between 1,000 and 2,000 l/ha. After three weeks, the degree of damage to the plants was determined and characterized by the values 0 – 5, which have the following meaning:

0—no effect
1—a few slightly burnt spots
2—marked damage to leaves
3—some leaves and parts of stalks partially dead
4—plant partially destroyed
5—plant completely dead The active compounds, the amounts used and the results can be seen from the table which follows:

Table A

| Active compound | Post-emergence test Amount of active compound used, kg/ha | A | B | C | D | E | F | G | H | I | J | K | L |
| --- | --- | --- | --- | --- | --- | --- | --- | --- | --- | --- | --- | --- | --- |
| 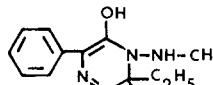 (14) | 2 | 5 | 5 | 5 | 5 | 5 | 5 | 5 | 5 | 4–5 | 4–5 | 4 | 4–5 |
| | 1 | 4 | 5 | 5 | 5 | 5 | 5 | 5 | 5 | 4 | 2 | 2 | 4–5 |
| | 0.5 | 4 | 5 | 5 | 3 | 4–5 | 5 | 4 | 3 | 3 | 1 | 2 | 3 |
| | 0.25 | 4 | 4–5 | 5 | 2 | 3 | 5 | 4 | 3 | 2 | 1 | 1 | 3 |
| 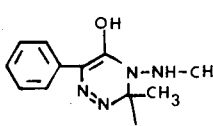 (1) | 2 | 5 | 5 | 5 | 5 | 5 | 5 | 5 | 5 | 4 | 5 | 3 | 5 |
| | 1 | 4–5 | 5 | 5 | 5 | 5 | 5 | 5 | 5 | 4 | 3 | 3 | 4–5 |
| | 0.5 | 4–5 | 5 | 5 | 5 | 4–5 | 5 | 5 | 5 | 2 | 2 | 3 | 4–5 |
| | 0.25 | 4 | 4 | 5 | 4 | 4 | 5 | 5 | 5 | 1 | 0 | 1 | 2 |
| 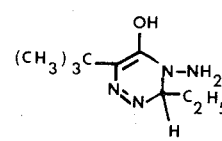 (10) | 2 | 5 | 5 | 5 | 5 | 5 | 5 | 5 | 5 | 5 | 5 | 4 | 5 |
| | 1 | 5 | 5 | 5 | 5 | 5 | 5 | 5 | 5 | 5 | 5 | 3 | 5 |
| | 0.5 | 4–5 | 5 | 5 | 5 | 5 | 5 | 5 | 3 | 3 | 4 | 3 | 4–5 |
| | 0.25 | 3 | 4–5 | 5 | 5 | 5 | 5 | 3 | 3 | 3 | 3 | 2 | 4 |

A Echinochloa
B Chenopodium
C Sinapis
D Galinsoga
E Stellaria
F Urtica
G Matricaria
H Daucus
I Oats
J Cotton
K Wheat
L Beans

EXAMPLE B

Pre-emergence test

Solvent: 5 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was then diluted with water to the desired concentration.

Seeds of the test plants were sown in normal soil and, after 24 hours, watered with the preparation of the active compound. It was expedient to keep constant the amount of water per unit area. The concentration of the active compound in the preparation was of no importance, only the amount of active compound applied per unit area being decisive. After three weeks, the degree of damage to the test plants was determined and characterized by the values 0–5, which have the following meaning:

0—no effect
1—slight damage or delay in growth
2—marked damage or inhibition of growth
3 heavy damage and only deficient development or only 50% emerged
4—plants partially destroyed after germination or only 25% emerged
5—plants completely dead or not emerged The active compounds, the amounts applied and the results obtained can be seen from the following table:

It will be appreciated that the instant specification and examples are set forth by way of illustration and not limitation, and that various modifications and changes may be made without departing from the spirit and scope of the present invention.

What is claimed is:

1. 3,4-Dihydro-1,2,4-triazine compound of the formula

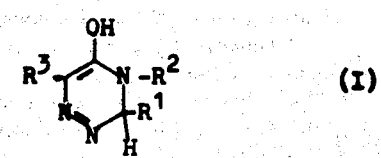

wherein
$R^1$ is alkyl of up to six carbon atoms or cycloalkyl of from three to six carbon atoms;
$R^2$ is methyl, amino, alkylideneamino, methylamino, β-hydroxyethylamino, 2-furylmethylamino, aralkylamino of up to 12 carbon atoms or substituted aralkylamino of up to 12 carbon atoms wherein the substituents are selected from lower alkyl; and
$R^3$ is alkyl of up to four carbon atoms or aryl of up to 10 carbon atoms or substituted aryl of up to 10 carbon atoms in the aryl moiety wherein the substituents are selected from alkyl of from one to four carbon atoms, halogen, haloalkyl, nitro and phenoxy.

2. 3,4-Dihydro-1,2,4-triazine compound as claimed in claim 1 wherein $R^1$ is alkyl of from one to four carbon atoms.

Table B

| Active compound | Pre-emergence test Amount of active compound used, kg/ha | A | B | C | D | E | F | G | H | I | J | K |
|---|---|---|---|---|---|---|---|---|---|---|---|---|
| (14) | 10 | 5 | 5 | 5 | 5 | 5 | 5 | 4 | 3 | 3 | 5 | 2 |
|  | 5 | 5 | 5 | 5 | 5 | 5 | 5 | 3 | 2 | 2 | 4–5 | 2 |
|  | 2.5 | 4 | 4–5 | 5 | 4 | 5 | 5 | 3 | 2 | 2 | 3 | 1 |
|  | 1.25 | 3 | 4–5 | 5 | 4 | 5 | 4–5 | 2 | 1 | 2 | 2 | 0 |
| (1) | 10 | 5 | 5 | 5 | 5 | 5 | 5 | 4 | 4 | 4 | 4–5 | 2 |
|  | 5 | 5 | 5 | 5 | 5 | 5 | 5 | 3 | 3 | 3 | 4 | 2 |
|  | 2.5 | 4 | 5 | 5 | 5 | 5 | 5 | 2 | 3 | 3 | 4 | 2 |
|  | 1.25 | 3 | 5 | 4–5 | 5 | 5 | 5 | 0 | 1 | 3 | 1 | 1 |
| (10) | 10 | 5 | 5 | 5 | 5 | 5 | 5 | 5 | 5 | 4 | 4–5 | 4 |
|  | 5 | 5 | 5 | 5 | 5 | 5 | 5 | 5 | 4–5 | 4 | 4–5 | 4 |
|  | 2.5 | 5 | 5 | 5 | 5 | 5 | 5 | 4–5 | 4 | 4 | 4 | 3 |
|  | 1.25 | 5 | 5 | 5 | 5 | 5 | 5 | 4–5 | 4 | 4 | 3–4 | 3 |

A Sinapis
B Echinochloa
C Chenopodium
D Lolium
E Stellaria
F G Oats
G Oats
H Cotton
I Wheat
J Buckwheat
K Corn 3. 3,4-Dihydro-1,2,4-triazine compound as claimed in claim 1 wherein $R^1$ is cycloalkyl of from three to six carbon atoms.

4. 3,4-Dihydro-1,2,4-triazine compound as claimed in claim 1 wherein $R^2$ is methyl.

5. 3,4-Dihydro-1,2,4-triazine compound as claimed in claim 1 wherein $R^2$ is amino, methylamino or hydroxyethylamino.

6. 3,4-Dihydro-1,2,4-triazine compound as claimed in claim 1 wherein $R^2$ is alkylideneamino.

7. 3,4-Dihydro-1,2,4-triazine compound as claimed in claim 1 wherein $R^2$ is 2-furylmethylamino.

8. 3,4-Dihydro-1,2,4-triazine compound as claimed in claim 1 wherein $R^2$ is aralkylamino.

9. 3,4-Dihydro-1,2,4-triazine compound as claimed in claim 1 wherein $R^2$ is substituted aralkylamino.

10. 3,4-Dihydro-1,2,4-triazine compound as claimed in claim 1 wherein $R^3$ is alkyl of from one to four carbon atoms.

11. 3,4-Dihydro-1,2,4-triazine compound as claimed in claim 1 wherein $R^3$ is aryl.

12. 3,4-Dihydro-1,2,4-triazine compound as claimed in claim 1 wherein $R^3$ is substituted aryl.

13. 3,4-Dihydro-1,2,4-triazine compound as claimed in claim 1 designated 5-hydroxy-3-methyl-4-methylamino-6-phenyl-3,4-dihydro-1,2,4-triazine.

14. 3,4-Dihydro-1,2,4-triazine compound as claimed in claim 1 designated 4-amino-3-ethyl-5-hydroxy-6-tert.-butyl-1,2,4-triazine.

15. 3,4-Dihydro-1,2,4-triazine compound as claimed in claim 1 designated 5-hydroxy-3-ethyl-4-methylamino-6-phenyl-3,4-dihydro-1,2,4-triazine.

16. Process for preparing a 3,4-dihydro-1,2,4-triazine compound of the formula

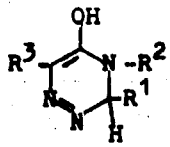

(I)

wherein $R^1$ is alkyl of up to six carbon atoms or cycloalkyl of from three to six carbon atoms;

$R^2$ is methyl, amino, alkylideneamino, methylamino, β-hydroxyethylamino, 2-furylmethylamino, aralkylamino of up to 12 carbon atoms or substituted aralkylamino of up to 12 carbon atoms wherein the substituents are selected from lower alkyl; and $R^3$ is alkyl of up to four carbon atoms or aryl of up to 10 carbon atoms or substituted aryl of up to 10 carbon atoms in the aryl moiety wherein the substituents are selected from alkyl of from one to four carbon atoms, halogen, haloalkyl, nitro and phenoxy;

which process comprises reducing a 1,2,4-triazine-5-one compound of the formula

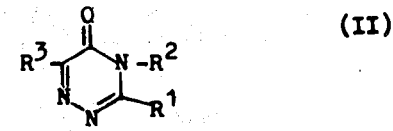

(II)

wherein $R^1$, $R^2$ and $R^3$ are defined as above with sodium borohydride in the presence of a polar solvent at a temperature from −10°C to 25°C.

17. Process as claimed in claim 16 wherein the reaction temperature is between −5°C and 10°C.

18. Process as claimed in claim 16 wherein said polar solvent is an ether or an alcohol.

19. Process as claimed in claim 18 wherein said ether or alcohol is selected from dioxane, tetrahydrofuran, methanol and ethanol.

20. Process as claimed in claim 16 wherein 1 to 1.2 moles of sodium borohydride are employed per mole of 1,2,4-triazin-5-one (II).

* * * * *